(12) United States Patent
Seppälä et al.

(10) Patent No.: US 6,290,982 B1
(45) Date of Patent: Sep. 18, 2001

(54) PLASTICIZABLE IMPLANT MATERIAL AND METHOD FOR PRODUCING THE SAME

(75) Inventors: Jukka Seppälä, Helsinki; Petri Orava, Espoo, both of (FI)

(73) Assignee: JVS-Polymers Oy, Espoo (FI)

( * ) Notice: Subject to any disclaimer, the term of this patent is extended or adjusted under 35 U.S.C. 154(b) by 0 days.

(21) Appl. No.: 09/331,047
(22) PCT Filed: Dec. 16, 1997
(86) PCT No.: PCT/FI97/00786
 § 371 Date: Jun. 16, 1999
 § 102(e) Date: Jun. 16, 1999
(87) PCT Pub. No.: WO98/26814
 PCT Pub. Date: Jun. 25, 1998

(30) Foreign Application Priority Data

Dec. 17, 1996 (FI) ......................................................... 965067

(51) Int. Cl.$^7$ ................................. A61F 2/02; A61K 47/30
(52) U.S. Cl. .......................................... 424/426; 514/772.3
(58) Field of Search ........................... 514/772.3; 424/426

(56) References Cited

U.S. PATENT DOCUMENTS 4,595,713  6/1986  St. John ............................... 523/105

FOREIGN PATENT DOCUMENTS

0628587 A2  12/1994  (EP).
0747072 A2  12/1996  (EP).

*Primary Examiner*—Carlos A. Azpuru
(74) *Attorney, Agent, or Firm*—Kubovcik & Kubovcik

(57) ABSTRACT

A plasticizable implant material for injection into the human body. The implant material is prepared through simultaneous selection of the comonomer ratio of ε-caprolactone and lactide and production parameters to provide a (co)polymer having an average molecular weight and caprolactone concentration that produces a phase transition temperature from solid to fluid within a temperature range of 37–55° C., preferably within the range of 43–48° C. When the temperature of the implant material is regulated to be within said range it can easily be transported to and placed at its target in the body by using a fluid transport and dosing device like a syringe or a heated press.

13 Claims, 4 Drawing Sheets

Fig. 1

PLASTICIZABLE IMPLANT MATERIAL AND METHOD FOR PRODUCING THE SAME

BACKGROUND OF THE INVENTION

During the last years in the biomedical applications synthetic implant materials have been taken into use to an ever-increasing degree. Biomaterial is defined to be a synthetic structural material whose aim is to interact with the biological system, and to replace, to treat, promote healing and renewal of and to join tissue, organs or some function of the body. Applications of these materials are reviewed in a publication edited by Höcker et al. (Macromolecular Symposia, vol. 103, January 1996, Klee, D., Severich, B., Höcker, H., pp. 19–29). Among the most important present and future applications are fixation materials of different types for bone fracture treatment which can be used for manufacturing screws, nails or rods for the above mentioned application, just to mention an example. These materials can be either non-biodegradable ones, e.g., metals or metal alloys, or polymeric materials degradable at a controlled rate in the body.

The most widely used biodegradable materials are high molecular weight lactide homopolymers, and lactide copolymers with, for example, glycolide. Useful parts or products are processed from these materials with processing methods for thermoplastics known in polymer technology, such as injection molding, hot pressing or extrusion.

Dentistry is well familiar with polymeric materials, too. Typical polymeric dental filling materials are chemically (for example, photochemically) curable plastics based on methyl methacrylate, dimethyl acrylate and their derivatives.

Fixation bone cements for orthopedic hip prostheses are also based on monomer combinations methacrylate type. In these applications the curing is based on redox initiated free radical polymerization, and on thus accomplished cross-linking and network formation.

The methacrylate based implant materials are, however, neither biodegradable nor biocompatible to any particular extent, as Dr. Heikkilä reports in his dissertation (Annales Universitatis Turkuensis Ser. D: Medica-Odontologica, tom. 240, 23.8. 1996, Turku/Finland, Heikkilä, J., Bioactive glass as a bone substitute in experimental and clinical bone defects, pp. 1–97, especially on p. 30).

In the use of methacrylate based implant materials further problems are caused by the exposition of personnel to volatile compounds, and the heat released during the reaction which may lead to an excessive local temperature increase, and to tissue damages as a consequence.

Another application for synthetic implant materials is controlled release of drugs or other bioactive substances when the idea is that the potent agent is released at a controlled rate from the polymeric matrix. As an example of this kind of application one can mention Norplant, a product brand and a trade mark of Leiras Co., which is based on a non-degradable polymeric material. A definitely formed device is implanted into the body by a surgical operation, and it is removed therefrom in a similar manner after a defined time when the active component has been released and diffused to the body.

Specific needs for development in the present state of the art are connected to the following areas:

Biocompatibility

If the material is not biocompatible it may induce tissue inflammation, unwanted cell growth, or rejection. Biocompatibilities of the presently used bone cements based for the most part on poly(methyl methacrylate) are unsatisfactory. This causes a certain risk of loosening of the hip prosthesis even in the case that there exists connective tissue formation between the polymeric material and bone tissue. A better biocompatibility would be a significant benefit for these materials.

Bioactivity

A bioactive implant material makes possible an active interaction between the tissue and the implant. As an example can be taken a mechanism by which the tissue is enabled to reconstruct into the implanted material while the implanted material itself is gradually removed due to biodegradation. Heimke, G. and Griss, P. have in their publication (Tissue interactions to bone replacement materials, in Bioceramics of calcium phosphate, de Groot, K. (ed.), 1983, CRC Press, Boca Raton Fla., pp. 79–97) characterized the concept of bioactivity, and have been cited by Heikkilä in his publication (FIG. 1 in the publication cited on page 1 where a) bioincompatible materials, b) bioinert but by the interface biocompatible materials, and c) bioactive and biocompatible materials are presented schematically. In the case a) the implant is tolerated but no connection with bone is formed, in the case b) intimate contact without bone bonding occurs at the interface whereas in the case c) both intimate contact with chemical bone bonding and gradual transformation between bone and implant material will result).

Bioactive materials have scarcely been reported in the literature. Especially in the case of bone cements bioactivity would be desirable and a significant benefit.

Controlled Biodegradation

Depending on the application and purpose of implant materials, they are expected to have either long lasting durability or controlled degradability in the body at a predetermined rate to harmless degradation products. The wanted degradation rate is depending substantially on the renewal rate of the tissue. In the case of bone tissue, it may be case of several months, or even of a time span in the range of half an year to one year.

In the case of controlled drug delivery it is crucial what is the desired rate of release of the active ingredient from the biodegradable matrix. When the potent ingredient release is based on matrix degradation the rate of matrix degradation determines the release rate of the drug. When active agent is released from the matrix through diffusion, degradation of the matrix shall happen mainly only after the release of the active agent.

Industrial Hygienic Aspects

The materials in continuous clinical use have to be safe to the users in a sense of work safety and hygiene. This is a severe drawback with the present bone cements and dental filling materials which are based on methacrylates.

Controlled Mechanical Properties

The mechanical properties required from implant materials are depending on the application. With bone implants usually a compression strength of at least 50 Mpa is necessary, as well as bending strength and tensile strength values which are at the level of those of bone. On the other hand, even in the bone applications, in case of bone grafting by filling of fractures and cavities, one can fairly well apply implant materials of lower strength if only the use properties, mouldability, biocompatibility, and possible biodegradability are at an optimum level.

In connection with soft tissue the requirements, on the other hand, are elasticity, flexibility and softness.

Plasticizability and Hardening Thereafter

The today used polymeric implant materials are either pieces of definite shape, i.e., processed before implanting to the final form using methods known in the plastics technology (as an example one can mention biodegradable bone nails based on polylactide, e.g., trade name Biofix), or bone cements based on methacrylate which typically have no biodegradability and lack bioactivity but as monomers, or as a blend of monomers, can be shaped in the target according to the needs, and can be hardened thereafter.

In surgery there would be plenty of applications for plasticizable, and afterwards to solid curable biodegradable polymeric materials. Then the idea is, that the material is plastic in connection to the surgical operation, and can be shaped according to the target's shapes or can be forced to penetrate even into small cavities, fractures and pores. Thereafter it again reversibly becomes solid, mechanically tough material which, however, has the property of controlled degradation. Thus plasticizable material can then be of the type of wax, plastic or rubber.

Better biocompatibility, bioactivity and wished mechanical properties as combined to the mouldability in the target and hardening occurring thereafter are properties which before the present invention have not been known in the state of the art.

Applicability to the Matrix of Bioactive Components

As examples of a bioactive active agent in an implant material can be mentioned different drugs, hormons or components activating tissue growth, such as hydroxyapatite in connection with bone tissue, and certain proteins.

The matrix has to be such a material that the appropriate hormons can be easily blended with it to form a homogeneous mixture. Especially the upper temperature in this process is often limited because many drugs and hormons are heat sensitive.

Easiness in Application (Usability and Transferability to the Target)

The implant material is placed to the target in connection to a clinical situation, e.g., in connection to an operation. Then the applicability and the mouldability of the material has to be easy: it must be possible to, for example, inject it, or to place it with a special press, to the target, and its hardening has to have a certain induction period during which the material can be shaped. On the other hand, one has to take into account that the possible drug present and/or the contact with tissue do not allow use of methods where the temperature even for a short period exceeds the typical upper limit of 55° C. The invention now present brings a novel solution which significantly improves applicability of biodegradable implants, for example, in regenerating surgery and in long lasting drug theraphy.

SUMMARY OF THE INVENTION

In comparison with the present state of the art, it has been possible according to the present invention surprisingly to achieve such a method which brings a significant improvement to it and opens up new possibilities in the use of body implantable polymeric materials. More specificly it has been possible to find such a composition of materials and a method, which enables the combination of several of the important properties in an exceptionally beneficial way from many applications' point of view. Below the invention's characteristic features are explained more in detail through examples which describe one successful way of its implementation.

The developed material is based on as such known structural units used in syntheses of polymeric biomaterials, and on structural units derived from capronic acid. Structural units derived from lactic acid can be, in addition to lactic acid itself, L- , D-, and DL-lactide units. Structural units derived from capronic acid can be, e.g., $\epsilon$-caprolactone. In addition as structural units can be organic carbonates, like trimethylenecarbonate.

Lactones are cyclic esters based on hydroxyacids. Some of the most common lactones are L-lactide, DL-lactide, D-lactide and E-caprolactone. With these to the same group of cyclic monomers can also be included cyclic carbonates, like trimethylenecarbonate.

The polymerization of lactones and cyclic carbonates can be carried out, as is well known. through catalytic ring opening polymerization. The catalyst used is typically some organometallic compound like tin(II)octoate (in other words stannous-2-ethylhexenoate), or trimethylaluminium.

The molecular weight control in this type of polymerization is based on the optimal selection of polymerization temperature and time, and it is possible also using so called initiator compounds, of which typical are multifunctional alcohols, e.g., glycerol. During the polymerization the polymer chains will start to grow from the —OH groups so that the molecular weight will be the lower the more initiator is present. By choosing the structure of the multifunctional alcohol the shape of the forming molecule can be affected. So, for example, glycerol forms a comb-like and pentaerythritol a star-shaped molecular structure, respectively.

The ring-opening polymerization of lactones is described, for example, in the following publication: Ylikangas, I., The polymerization of $\epsilon$-caprolactone with stannous catalysts, *Polyemer Technology Publication Series* No. 15, Helsinki University of Technology, 1993, 1–23.

Thus it is as such known that by using the above mentioned structural units one can form a biodegradable polymeric material which has either plastic-like or rubbery properties but in the present invention the structural units are used in a special way to achieve a biodegradable polymeric material which melts within a certain narrow temperature range and which, on the other hand, is either a mechanically tough plastic, a wax or a rubbery material below its melting temperature. In respect of implant application it is important that the material melts or plasticizes at a temperature which is somewhere 3–12° C. above the body temperature, and becomes again a solid material at a temperature still above the body temperature. The melting and plasticization temperature of the material must, of course, not to be too high in respect to the body temperature, taking into account the above described temperature resistance of tissue and of drug-like active agents. When melting or plasticizing the material according to the invention becomes a viscose mass or fluid which can be shaped, injected or otherwise used to fill hollows, fractures and cavities as well as to replace different kinds of tissue defects, as in bone grafting.

In the present invention it has become possible to adjust the temperature at which the material becomes plastic to within the temperature range of 42–55° C., or it can be adjusted to any temperature around this temperature range as well. The melting temperature of the material can be checked by means of measurements of entalphy changes, using differential scanning calorimetry (DSC) as the method.

The control of the melting temperature of a polymeric material according to the invention is based on one hand on the specific monomer ratio selection in the starting materials, and, on the other hand, on the specific control of the molecular weight in the copolymerization.

Both factors together namely affect the melting temperature of the copolymer, hence only certain combinations of them bring about the wished result. FIG. 1 is a graphical presentation the combinations of monomer compositions and average molecular weights for the L-lactide/caprolactone copolymers which produce a suitable melting temperature for implant use, indicated by points falling within the shaded area between curves in the monomer molar ratio versus molecular weight coordination.

In several applications it is wanted that the implanted material is degradable in a controlled manner, or vice versa mechanically stable at least for a certain period of time. The first stage in bidegradation of the materials according to the present invention is hydrolysis which splits polymer chains to shorter segments until the molecular size is at a level where the own enzymatic functions of the body can convert the degradation products to compounds which are natural in the body.

The hydrophilic character of the polymer is an essential parameter affecting the degradation rate. Thus in copolymers of the present invention it is possible to control hydrolytic degradation rate through control of monomer composition, and so also hydrophilic character, which according to what has been presented above directly affects the degradation rate of the material in the body. One has to note, however, that the exact rate of the degradation in the body depends on the end use, and has to be always investigated case by case. FIG. 2 indicates the dependence between the hydrolysis rate and monomer composition in the L-lactide/ε-caprolactone copolymers prepared in the examples.

An essential feature of the invention is that if the composition of the material comprises only or for the most part ε-caprolactone, the rest being L-lactide, DL-lactide, D-lactide or trimethyl carbonate, the polymer is almost stable in the body, or degrades very slowly, typically during several years. Through selection of the monomer composition keeping this in mind, and through adjusting the molecular weight of the forming polymer by controlling the polymerization parameters, one can get benefit from the well-known biocompatibility and bioactivity of poly(hydroxy acid)s. On the other hand, a waxy version of the copolymers according to the invention can be made to degrade even really fast, just by controlling both average molecular weight and monomer composition as described above. In that case the degradation rate in the body is typically from some days to some weeks.

A material according to the invention is in a molten state, i.e., while being at a temperature exceeding 37° C., preferably within a temperature range from 42 to 55° C., and most preferably within a temperature range from 43 to 48° C., a plastic mass or a viscous fluid. This makes it possible to shape the material by hand or by using specific tools to a desired shape to meet the needs of the target, or alternatively makes it possible that the material can, by different transportation methods, be used to fill different and variably shaped spaces, hollows, cavities and fractures numerously existing in surgery, dentistry and medicine.

Especially advantegous in the invention is an unexpected observation that the plasticizable material according to the invention can above its melting temperature be in such a state that it can be applied to the target using a specific press, the schematic drawing of which is presented in FIG. 3. Said press essentially consists of a heated cylinder 3, a die 4 (which can be of different kinds according to the needs of the end uses), a piston 5, trigger 2, and a press mechanism 8. The temperature of the cylinder 3 can be regulated at a desired level by a thermostat so that the implantable material is either in a molten state or in a plasticized state inside the cylinder in front of the piston 5, and thus it can be transferred using the press device through the die to the target area. Because the temperature of the molten or plasticized polymeric material is higher than the body temperature but in any case such that there is no danger of tissue damage, the implant material can be transferred directly to the target area where it solidifies when cooling down.

Advantages of the method according to the invention are the simplicity for the user, e.g., for the surgeon, hygienicity because the implant material is all the time in a closed chamber, and the point that there are no volatile components utilized in the method (an advantage in respect of industrial hygiene and working safety), and further that there is no heat generation in connection with the solidification (as usually is the case in the solidification of bone cements) and the risk of tissue damages can thus be avoided. As an additional benefit one can mention that by using differently shaped longer dies 2 it becomes possible to inject the mass to narrow, deep and variously shaped channels to their very end or to their deepest points, to fractures, to cavities and the like as target areas.

Another preferred embodiment of the implantation method according to the invention is the use of such a device which does not contain any specific piston, but the piston 5 is replaced with a rod made up of polymeric material according to the invention which penetrates through the unheated part of the cylinder to the heated part where it melts or plasticizes. The feeding mechanism 8 pushes the rod into the cylinder, and correspondingly the molten or plasticized polymeric material is extruded out through the die 4.

Still one advantageous method to implantate according to the invention is the one where the temperature of the cylinder 3 is raised above one hundred degrees centigrade and is held there for the time required for completing heat sterilization. In this case any separate sterilization is not needed, and the sterilized material remains in its closed space sterile and ready for use. Naturally this form of implantation can be applied provided that there are no heat sensitive active agents, for example drugs, present as blend components. After the sterilization treatment the material is allowed to cool down to the temperature range of 37–55° C. so that it remains both sterile and in a molten or plasticized state for the implanting.

One specific way of implantation is the one where the polymer according to the invention is produced in a way that its melt viscosity is low enough to allow its injection to the target area with a suitable injection syringe. In this case the polymeric material when cooled down to its solid state at the body temperature is a waxy material.

The implant material according to the present invention can be applied in a way that the material forms a matrix in the controlled release of drugs, or it forms a matrix in blends containing bioactive inorganic materials where the bioactive component can be selected from the group including, for example, hydroxyapatite, a filler based on coral, bone allocrafts or its particles, titanium particles and carbon fibers, just to mention some. In this form of application the blend component can, of course, also be soluble to the polymeric matrix, as is the case in connection with the most drugs. On the other hand, the solid components in the mixtures may be platelets or fibrous particles so that the composition is comparable to the polymer composites, and in which case the blend component essentially improves mechanical properties. A special advantage is achieved in the aspect that the use of a biodegradable polymeric matrix yields adhesion between particles, plasticizability, ease of processing, and improved biocompatibility to this kind of materials containing solid particles.

In connection with drugs, hormones, or other corresponding active agents, the method according to the invention enables the controlled release and targeted location to the body, for example, in connection with an operation, or by injecting.

Both composite materials containing solid fillers and/or reinforcements and blends containing soluble components can be located according to the invention, for example, as is presented in FIG. 3, easily and safely as a plastic mass or a viscous fluid directly to the end use target.

Furthermore it is characteristic for the method according to the invention that also other methods suitable for the dosing and transferring plastic masses and viscous fluids are suitable for use, and they are in accordance with the invention.

BRIEF DESCRIPTION OF THE DRAWINGS

FIG. 1 is a diagram representing the limits of average molecular weight versus (co)monomer concentration of a (co)polymer of $\epsilon$-caprolactone and/or a lactide of the present invention having a physical state transition temperature from solid to liquid of 37° C. to 55° C.

DESCRIPTION OF PREFERRED EMBODIMENTS

EXAMPLES 1–14

The Used Chemicals

Figure 2:
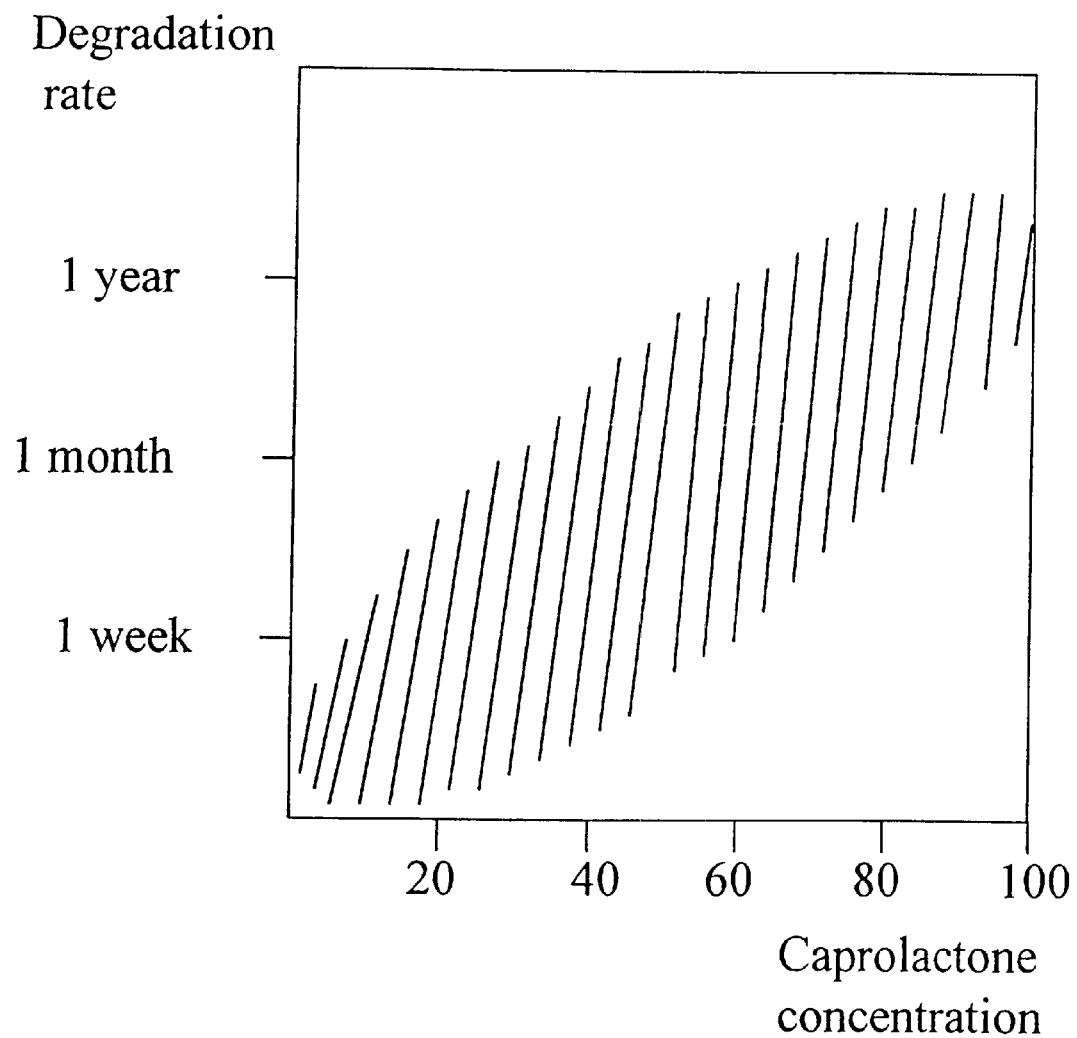
FIG. 2 is a diagram representing the degradation rate of (co)polymers of $\epsilon$-caprolactone and/or a lactide within the scope of the present invention.
Figure 3:
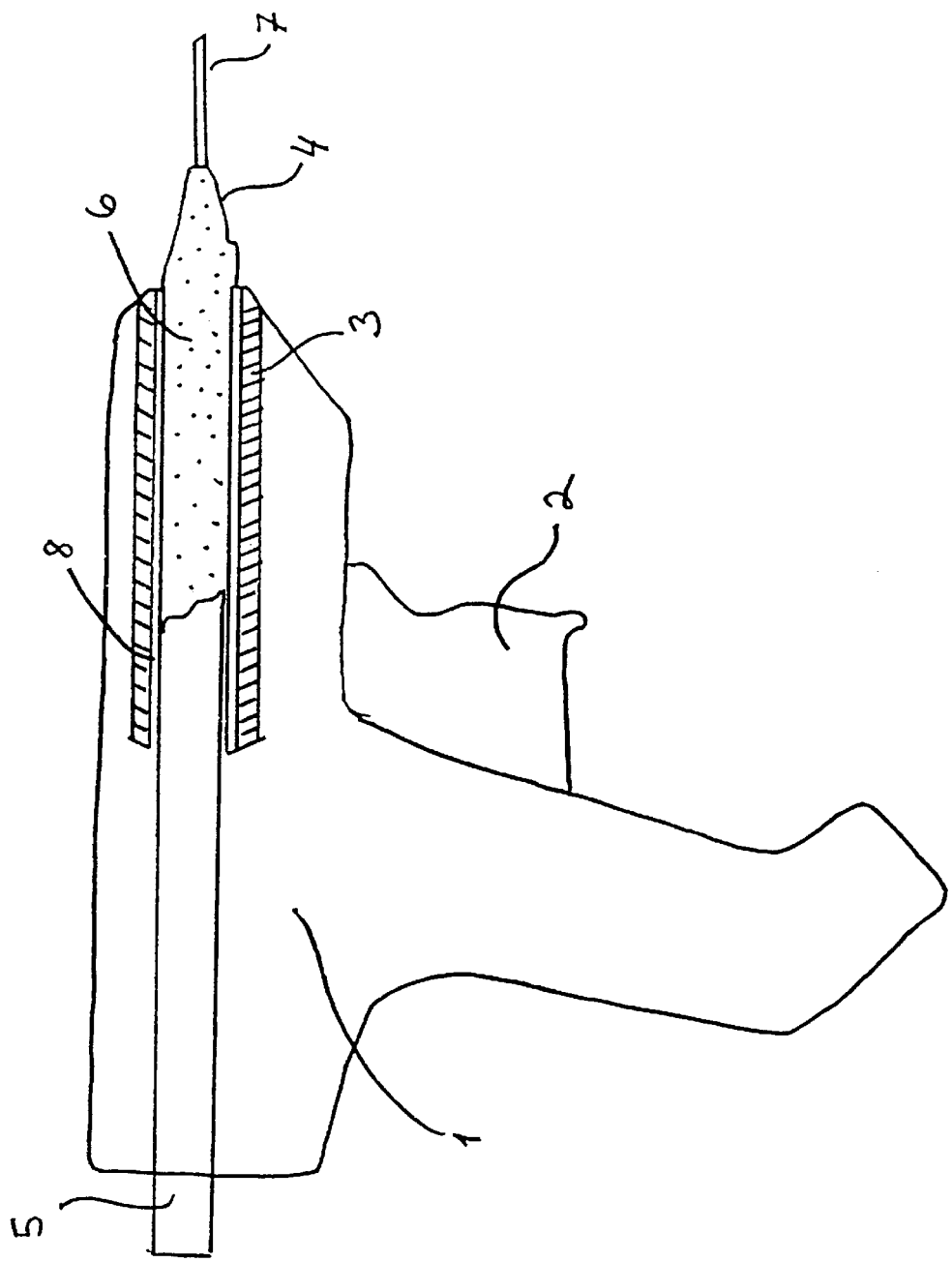
FIG. 3 shows a schematic drawing of a device for applying a (co)polymer of the present invention to a target area in the body.

The copolymers were prepared from $\epsilon$-caprolactone monomer ($\epsilon$-CL), >99% purity, Fluka Chemika nr. 21510, lot 335334/1 794, and D,L-lactide (D,L-LA), Purac, lot DF 386H. As catalyst was used tin(II)octoate (Stannous 2-ethylhexanoate; SnOct), 95% purity, Sigma nr. s-3252, lot 112H0248. As the initiator was used glycerol, 99,5% purity, Fluka BioChemika nr. 49767, lot 42489/2 1094.

The Purification and Storage of the Used Chemicals

In the used $\epsilon$-caprolactone there was molecular sieves (adding date 15.02.1995), and the bottle was stored in a dark place at a temperature of 23° C. The caprolactone was not distilled again.

D,L-lactide was purified with recrystallization from toluene (b.p. 110° C.) using a mass ratio of 1:2 toluene/lactide. The lactide dissolved to a hot toluene was poured from round bottom flask to a decanter. The lactide solubilized to the toluene was let to recrystallize overnight at 23° C. After filtration the crystallized lactide was dried under reduced pressure for 4 days at +40° C. and 4 mbar. The same stages were repeated once. In the polymerizations was thus used twice recrystallized D,L-lactide which was stored in an exsiccator in a refrigerator at +4° C. The tin octoate and the glycerol were used as such.

They were stored in a dark place at +23° C.

Preparations for Polymerization

At preceding night the used lactide has been placed into a vacuum chamber at +40° C. and 4 mbar. The two-piece polymerization reactor (volume about 0.7 liter) was assembled, and the condition of the Teflon gasket belonging to the reactor was checked. The proper closure of the upper part and the lower part of the reactor was ensured by a iron wire closing device. The male parts of the glass joints belonging to the reactor were wiped slightly with a vacuum grease.

Polymerization

The oil thermostat used for the reactor heating was regulated to 140° C. The oil temperature varies during a polymerization within 5° C. above and below the set temperature. Lactide was weighed first about 10 g into a small decanter (accuracy 0.0001 g). On the lactide the tin octoate and the glycerol was weighed using a Pasteur pipet. After this the decanter was poured into the reactor, and the rest of the lactide was weighed with another balance (accuracy 0.01 g). $\epsilon$-Caprolactone was then either poured or pipeted on lactide.

The magnetic agitator has been added to the reactor before the reactor halves were closed. The reactor was placed into a thermostat, and the agitation was adjusted to the speed of 250 1/min. The reactor was flushed with Argon (AGA, grade S, 99.99%) for about 15 min. Argon was fed to the reactor through a glycerol trap. Finally the outside of the reactor was wrapped with a aluminium foil. When the forming copolymer started to become more viscous the agitation speed was adjusted again to the speed of 125 l/min.

The Prepared Copolymers and their Analysis

Table 1 summarizes the copolymerizations and their results using $\epsilon$-caprolactone and D,L-lactide ($\epsilon$-CL/D,L-LA). In all the polymerizations the temperature was 140° C. and the polymerization time was 24 h (except in Example nr. 3 where it was 29 h). Molecular weights determined by gel permeation chromatography (GPC) are presented in Table 1 in terms of number average molecular weight Mn, weight average molecular weight Mw, and the polydispersity PD calculated as the ratio of the previous ones Mw/Mn. In the same Table 1 there are also presented the transition temperatures of the polymerization products. i.e., melting temperature Tm and glass transition temperature Tg, determined using differential scanning calorimetry (DSC).

GPC Measurements

The GPC-samples for molecular weight measurements were prepared by dissolution of 15 mg of sample into 10 ml of chloroform. As columns were used columns of Polymer Laboratories Ltd with pore diameters of 100–10000 Å. The used detector was RI-, i.e., refractive index detector, manufactured by Waters, and a 55 min run time with a flow rate of 1 ml/min were used. To determine the molecular weights of the samples were used polystyrene (PS) standards manufactured by Polymer Laboratories, and the calibration curve based on the same. Because there is no experimental Mark-Houwink constants a and K available, the molecular weights in the Table 1 are not absolute molecular weights for the samples but relative values in comparison with PS standards.

TABLE 1

| Example | ε-CL D,L-LA- ratio (M-%) | SnOct- conc. mol/ mol Σ monomers | Glycerol conc. mol/ mol Σ monomers | GPC results $M_n$ (g/mol) | $M_w$ (g/mol) | PD | DSC results $T_m$ (° C.) | $T_g$ (° C.) |
|---|---|---|---|---|---|---|---|---|
| 1 | 100/0 | 0.0001 | 0.005 | — | — | — | 56 | — |
| 2 | 80/20 | 0.0001 | 0.005 | 35000 | 50000 | 1.4 | 47 | — |
| 3 | 80/20 | 0.0001 | 0.005 | 40000 | 60000 | 1.5 | 42 | — |
| 4 | 80/20 | 0.0001 | 0.005 | 40000 | 60000 | 1.5 | 45 | — |
| 5 | 80/20 | 0.0001 | 0.0005 | 165000 | 272000 | 1.65 | 46 | −53 |
| 6 | 80/20 | 0.0001 | 0.25 | — | — | — | — | — |
| 7 | 100/0 | 0.0001 | 0.25 | 4300 | 5200 | 1.2 | 35 | — |
| 8 | 100/0 | 0.0001 | 0.05 | 445 | 729 | 1.6 | — | — |
| 9 | 100/0 | 0.0001 | 0.05 | — | — | — | — | — |
| 10 | 100/0 | 0.0001 | 0.25 | 2000 | 2600 | 1.3 | — | — |
| 11 | 100/0 | 0.0001 | 0.0125 | — | — | — | 53 | — |
| 12 | 100/0 | 0.0001 | 0.023 | 10000 | 12000 | 1.2 | — | — |
| 13 | 10010 | 0.0001 | 0.034 | — | — | — | 43 | — |
| 14 | 80/20 | 0.0001 | 0.25 | 1100 | 1400 | 1.3 | — | — |

DSC Measurements

Figure 4:
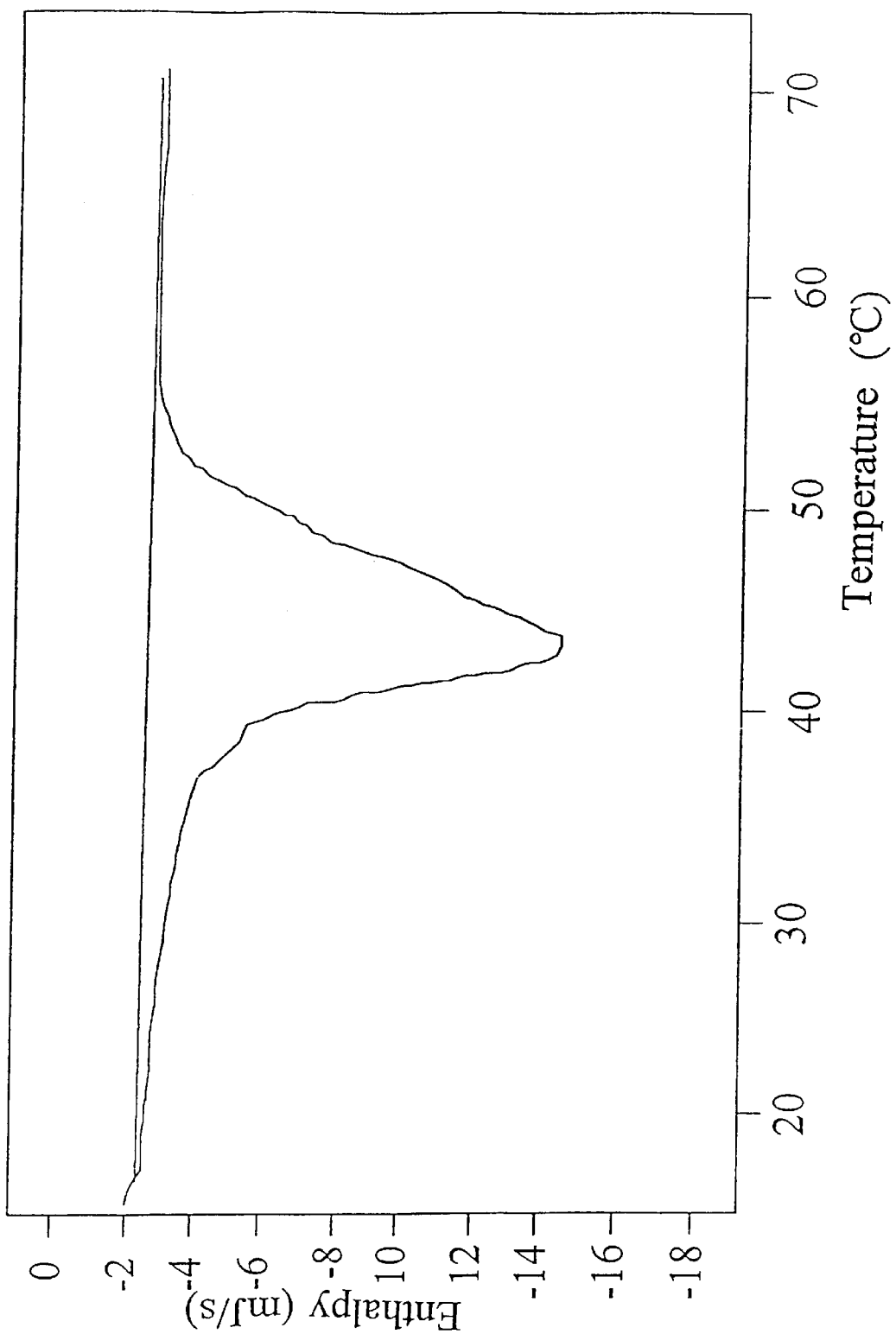
FIG. 4 is a DSC curve of the product of Example 3.

In the DSC measurements the 5–10 mg sample was heated with a rate of 10° C./min in a calorimeter chamber. In order to get a similar thermic history for all the samples, the samples were heated above their melting temperature to temperature of +80° C. and cooled down to about −50° C. The Tm and Tg values were determined from the curve recorded from the second heating, and they are presented in the Table 1. In FIG. 4 is presented the DSC curve of the product prepared in Example 3, which is typical for all the polymers according to the invention.

Figure 1:
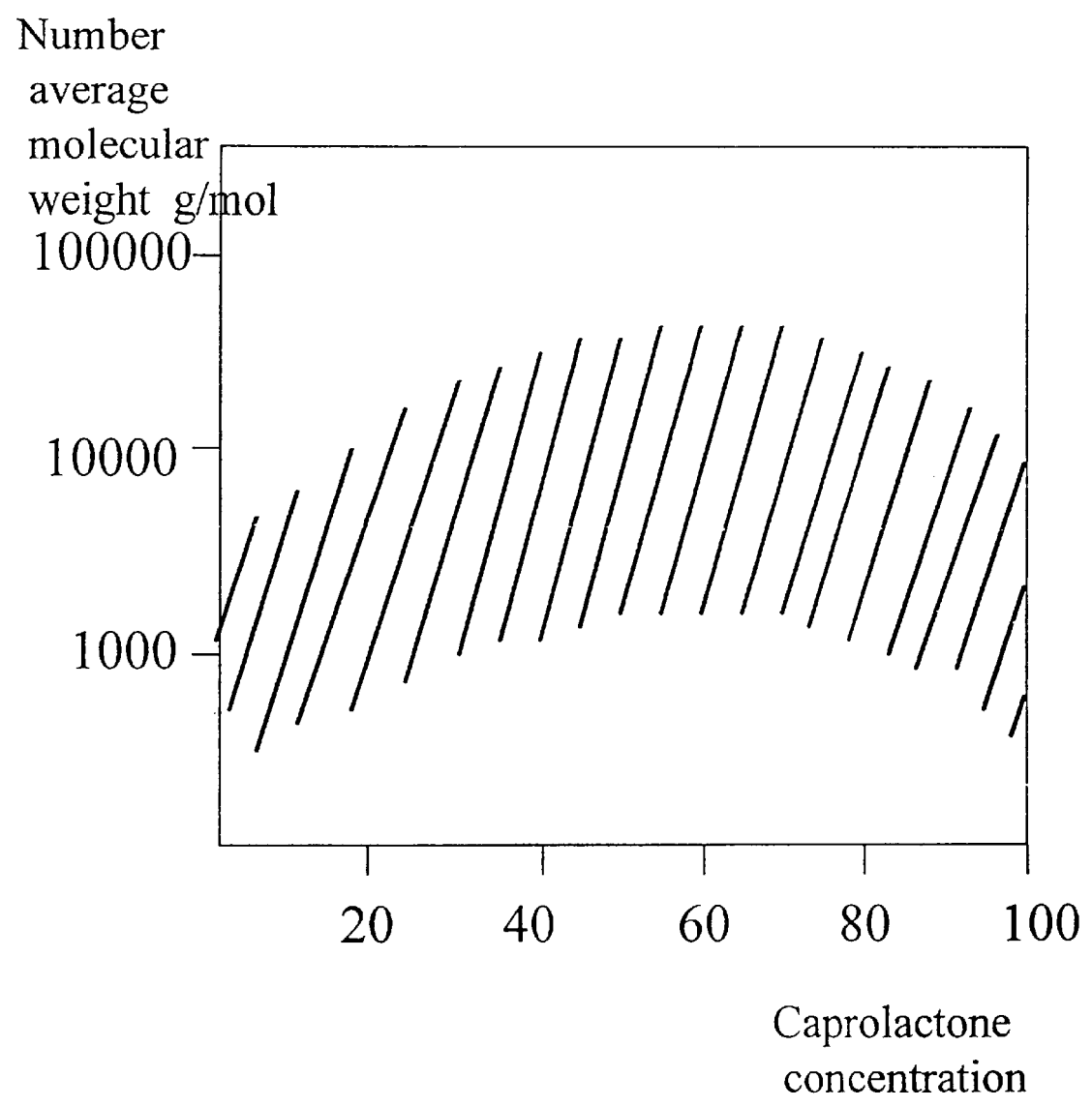

Presentation of the Characteristic Monomer Ratio-molecular Weight Dependence for ε-CL/D,L-LA Copolymers When the monomer ratio-molecular weight value pairs corresponding to the polymer products from Examples 1–14 (Table 1) and being suitable for implantation use are presented graphically in a right angle co-ordinate system, one can see that the hit points are located on the area between two curves (the shaded area in FIG. 1). It is apparently possible to adjust the properties of the implant material according to the invention, of which melt viscosity, degradation rate in the body and mechanical properties in a solid state are the most significant, by means of FIG. 1 based on Examples 1–4 by selecting suitable combinations of comonomer ratio and polymerization parameters (of which the concentration of the so called initiator compound can be mentioned here). It is self-evident to anyone skilled in the art that the method to regulate material properties described in the invention can also be used with other monomer combinations suitable for the production of biodegradable implant materials.

Examples 15–26

Dependence Between Biodegradability and Monomer Composition of ε-CL/D,L-LA Copolymers Plasticizable in the Range of Temperatures from 37 to 55° C.

The biodegradability of typical materials prepared in the manner described above was tested by hydrolysis experiments in a buffered aqueous solution at a temperature of 37° C. (Examples 15–26; Table 2). The change of sample weight was followed with time so that their degradation rate was demonstrated. The hydrolytic degradation is the first, and thus the limiting, stage in regard to biodegradation, and therefore reflects quite well the overall total degradation rate in vivo, too. Based on experimental results FIG. 2 illustrates the depedence between monomer composition and degradation rate in polymers according to the invention. Degradation rate of a polymer in certain conditions is affected not only by the composition and consequent differences in hydrophilic character but at least by the average molecular weight, and this is why also samples having the same composition may have different degradation rates. The values presented in Table 2 can be regarded as typical examples for the materials according to the invention. Naturally they do not, however, represent the only possible property combinations of the implant materials produced with the method according to the invention.

TABLE 2

| Example nr. | Composition ε-CL/lactide (M-%) | Molecular weight (g/mol) | Decomposition rate |
|---|---|---|---|
| 15 | 0/100 | 10 000 | 1 d |
| 16 | 10/90 | 10 000 | 2 d |
| 17 | 10/90 | 30 000 | 1 week |
| 18 | 20/80 | 10 000 | 2 d |
| 19 | 20/80 | 30 000 | 2 weeks |
| 20 | 40/60 | 10 000 | 3 d |
| 21 | 40/60 | 50 000 | 1 month |
| 22 | 60/40 | 10 000 | 5 d |
| 23 | 60/40 | 80 000 | 6–10 months |
| 24 | 80/20 | 20 000 | 3 weeks |
| 25 | 80/20 | 300 000 | 1 year |
| 26 | 100/0 | 80 000 | over 1 year |

What is claimed is:

1. A method of determining a material for implantation into a human body comprising experimentally establishing two curves in a diagram representing the average molecular weight versus (co)monomer concentration of a (co)polymer of ε-caprolactone and/or a lactide, said curves defining the limits of average molecular weight and comonomer concentration that provide a (co)polymer of ε-caprolactone and/or a lactide having a physical state transition temperature from solid to fluid of 37° C. to 55° C., and selecting a ratio of (co)monomer amounts and average molecular weight within the area bounded by said curves.

2. An implant material comprising a (co)polymer of ε-caprolactone and/or a lactide having an average molecular weight and caprolactone concentration within the shaded area of FIG. 1 and having a physical state transition temperature from solid to fluid of 37° C. to 55° C.

3. The method according to claim 1 wherein the area including the points in right angle coordination fixed by the possible comonomer ratio average molecular weight value pairs is bordered by two downwards opening curves which resemble parables.

4. The method according to claim 1 characterized by that transition temperatures at which the macromolecular copolymers prepared by the method change their physical state temporarily and reversibly from solid to fluid, in other words are plasticized, are preferably in the range from 4° C. to 18° C., most preferably from 6° C. to 12° C., higher than the normal body temperature, and in said or any higher temperature the prepared copolymers can be transferred as fluid.

5. The method according to claim 1 wherein the control of the average molecular weight of the copolymer is done by selecting the reaction component called initiator compound and its percentage in the reaction mixture.

6. The method according to claim 1 wherein the so called initiator compound is 1,2,3-propanetriol, also known as glycerol, the catalyst of the reaction being tin(II) 2-ethylhexanoate, also known as stannous octoate, and the mole ratio of the amount of the initiator compound to the total amount of monomers is in the range from 0.0005 to 0.01.

7. The method according to claim 1 wherein the reaction mixture contains trimethyl carbonate, also known as 1,3-dioxane-2-one.

8. The implant material according to claim 2 characterized by that the area of points in right angle coordination fixed by the possible value pairs comonomer composition versus average molecular weight is bordered by experimental curves which can be determined by preparing copolymers and analyzing their melting temperatures.

9. The implant material according to claim 2 characterized by that they are plasticizable by raising their temperature in a controlled manner to a temperature in the range from 2° C. to 20° C. higher than the body temperature to make them moldable by hand or by a tool or injectable by using a device suitable for extrusion of plastic masses or viscous fluids, and that at body temperatures they again solidifies to form a tough plastic, a wax or a rubbery material.

10. The implant material according to claim 2 characterized by that they are plasticizing at a temperature in the range from 37° C. to 55° C., preferably in the range from 43° C. to 48° C., and form at temperatures within or above said temperature ranges flowing masses or viscous fluids which can be molded or used to fill holes, spaces, fractures or cavities when the force for the transfer of the implant material is produced by a piston moving in a heated cylinder.

11. The implant materials characterized by that they are biodegradable at a controlled rate in body conditions.

12. The implant material according to claim 2 characterized by that their degradation rates in body conditions can be from some days to several years, and get any value between those limits.

13. The implant material according to claim 2 characterized by that they are comprised of an at a controlled rate biodegradable polymer matrix blended with drugs, hormones, or other active ingredients, or solid fillers or reinforcing agents such as hydroxyapatite, bone allografts or choral based material.

\* \* \* \* \*